United States Patent [19]

Schwestka-Polly

[11] Patent Number: 5,281,135

[45] Date of Patent: Jan. 25, 1994

[54] ARTICULATOR FOR CAST SURGERY AND METHOD OF USE

[76] Inventor: Rainer Schwestka-Polly, Am Kirschberge 24, 3400 Göttingen, Fed. Rep. of Germany

[21] Appl. No.: 998,813

[22] Filed: Dec. 30, 1992

[30] Foreign Application Priority Data

Dec. 31, 1991 [DE] Fed. Rep. of Germany ....... 4143252

[51] Int. Cl.$^5$ .......................... A61C 11/00; A61C 5/00
[52] U.S. Cl. ........................................ 433/56; 433/54; 433/215
[58] Field of Search ....................... 433/56, 54, 59, 68, 433/215

[56] References Cited

U.S. PATENT DOCUMENTS 4,189,835  2/1980  Seldin .................................. 433/215

FOREIGN PATENT DOCUMENTS 4018273  1/1991  Fed. Rep. of Germany .

OTHER PUBLICATIONS

"Positioning control of the upper incisors in orthognathic surgery" R. Schwestka European Journal of Orthodontics 13 (1991) 367–371.
Bell, et al, "Art and Science of the Le Fort I Downfracture", Int J Adult Orthod and Orthogn Surg 33: 23–52, 1988.
Ehmer, et al, "Calibrated Double Split Cast Simulations for Orthognathic Surgery", Int J Adult Orthod Orthognath Surg 33: 223–227, 1988.
Ellis, E., "Modified Splint Design for Two-Jaw Surgery", J Clin Orthod 16: 619–622, 1982.
Ellis III, E., "Accuracy of Model Surgery: Evaluation of an Old Technique and Introduction of a New One", J Oral Maxillofac Surg 48: 1161–1167, 1990.
Ellis III, et al, "A Method to Accurately Predict the Position of the Maxillary Incisor in Two-Jaw Surgery", J Oral Maxillofac Surg 42: 402–404, 1984.
Härle, F., "Le Fort I Ostectomy (Using Miniplates) for Correction of the Long Face", J Oral Surg 38: 427–432, 1980.
Henry CH, "Modified Boley Gauge for Use as a Reference Plane in Orthognathic Surgery", J Oral Maxillofacial Surg 48: 535–539, 1990.
Johnson, D. G., "Intraoperative Measurement of Maxillary Repositioning: an Ancillary Technique", Oral Surg Oral Med Oral Pathol 60: 266–268, 1985.
Kahnberg, et al, "Planning and Control of Vertical Dimension in Le Fort I Osteotomies", J Cranio-Max-Fac Surg 18: 267–270, 1990.
Luhr, et al, "Rigid Skeletal Fixation in Maxillary Osteotomies. Intraoperative Control of Condylar Position", Clin Plast Surg 16: 157–163, 1989.
Luhr, et al, "Intraoperative Control of Condylar Position in Maxillary Osteotomies with Rigid Skeletal Fixation", In: Bell WH (Hrsg): Modern Practice in Orthognathic and Reconstructive Surgery, Saunders, Philadelphia, at press.
Neubert, et al, "Refined Intraoperative Repositioning of the Osteotomized Maxilla in Relation to the Skull and TMJ", J Cranio-Max-Fac Surg 16:8–12, 1988.

(List continued on next page.)

Primary Examiner—Gene Mancene
Assistant Examiner—Cindy Cherichetti
Attorney, Agent, or Firm—Michael J. Striker

[57] ABSTRACT

An appliance for the three-dimensional adjustment of the maxillary cast is mounted by means of a screw on an articulated part. The appliance includes a first measuring element whose tip cooperates with a first reference point on a central incisor of the maxillary cast. The appliance includes also a second and a third measuring element whose tips correspond each with a further reference point on a first molar of the maxillary cast. Each of these measuring elements can be adjusted separately and three-dimensionally to the desired position by the special design of the appliance.

13 Claims, 5 Drawing Sheets

OTHER PUBLICATIONS

Ripley, et al, "A Composite Split for Dual Arch Orthognathic Surgery", J Oral Maxillofac Surg 40: 687–699, 1982.

Schwestka, et al, "Condylar Position Control During Maxillary Surgery: The Condylar Positioning Appliance and Three-Dimensional Double Splint Method", Int J Adult Orthod Orthognath Surg 5: 161–165, 1990.

Schwestka, et al, "Control of Vertical Position of the Maxilla in Orthognatic Surgery, Clinical Application of the Sandwich Splint", Int J Adult Orthod Orthognath Surg 5: 133—136, 1990.

Schwestka, et al, "Splint for Controlling Vertical Position in Maxillary Osteotomies", J Clin Orthod 24: 427–431, 1990.

Stanchina, et al, "A Comparison of Two Measures for Repositioning the Maxilla During Orthognathic Surgery", Int J Adult Orthod Orthognath Surg 33: 149–154, 1988.

Turvey, "Simultaneous Mobilization of the Maxilla and Mandible: Surgical Technique and Results", J Oral Maxillofac Surg 40: 96–99, 1982.

Turvey, et al, "Surgical–Ortodontic Treatment Planning for Simultaneous Mobilizaton of the Maxilla and Mandible in Correction of Dentofacial Deformities" Oral Surg Oral Med Oral Pathol 54: 491–498, 1982.

Van Sickels, et al, "Predictability of Maxillary Surgery: A Comparison of Internal and External Reference Marks", Oral Surg Oral Med Oral Pathol 61: 542–545, 1986.

Luhr, "Miniplate Fixation of Le Fort I Osteotomies". (Discussion to Rosen HM), Plast Reconstr Surg 78: 755, 1986.

Nishioka, et al, "Modified External Reference Measurement Technique for Vertical Positioning of the Maxilla", Oral Surg Oral Med Oral Pathol 64: 22 23, 1987.

ARTICULATOR FOR CAST SURGERY AND METHOD OF USE

BACKGROUND OF THE INVENTION

The present invention relates to a method of making a surgical splint as an aid to the positioning of a tooth-carrying maxillary segment which is to be mobilized following Le Fort I surgery.

More particularly it relates to such a method in accordance with which a maxillary cast and a mandibular cast of a pair of casts of the patient made at least approximately in the ratio 1:1 are centered in an articulated manner in an articulator with reference to the jaw hinge and are thereby adjusted into the pre-operative dental position, the maxillary cast is mobilized, the mobilized maxillary cast is adjusted three-dimensionally in the articulator into the desired post-operative dental situation relative to the pre-operative planned position of the upper lip of the patient and relative to the rest of the pair of casts, and on the basis of the relative adjustment of maxillary cast and mandibular cast achieved according to the preceding step the surgical splint is made in a gap between maxillary cast and mandibular cast for analogous intra-operative use.

One method of this type is disclosed for example in the German reference DE 4,018,273 A1. In this method the adjustment of the mobilized tooth-carrying maxillary segment 30 takes place in a manner known per se, after a Le Fort I model operation has been carried out.

In maxillary orthodontic-surgical treatment, after the Le Fort I osteotomy, a three-dimensional readjustment of the maxilla is possible. The maxilla of the patient is positioned in the new position by means of a surgical splint and is fixed with osteosynthesis wires or with mini-plates. During the treatment planning, during the cast surgery and during the surgery itself it is particularly important to maintain an exact position of the upper incisors in relation to the upper lip and to maintain an exact position of the whole maxilla in relation to the rest of the skull including the jaw hinge (Härle, F., Le Fort I ostectomy (using miniplates) for correction of the long face. J. Oral Surg. 38: 427–432, 1980; Zürcher A., Hardt N., Steinhäuser, E. W., Interokklusaler Splint als Rezidivprophylaxe bei totalen Unterkieferosteotomien. Fortschr. Kiefer Gesichtschir. 26: 81–82, 1981; Ellis E., Modified splint design for two-jaw surgery. J. Clin. Orthod. 16: 619–622, 1982; Ripley, J. F., Steed, D. L., Flanary C. M., A composite splint for dual arch orthognathic surgery. J. Oral Maxillofac. Surg 40: 687–688, 1982; Turvey, T. A., Hall, D. J., Fish, L. C., Epker, B. N., Surgical-orthodontic treatment planning for simultaneous mobilization of the maxilla and mandible in correction of dentofacial deformities. Oral Surg. Oral Med. Oral Pathol. 54: 491–498, 1982; Luhr, H. G., Miniplate fixation of Le Fort I osteotomies. (Discussion to Rosen, H. M.). Plast Reconstr. Surg. 78: 755, 1986; Somsiri, S. T., Das Doppelsplintverfahren zur Vorbereitung einer simultanen chirurgischen Lagekorrektur des Ober- und Unterkiefers. Fortschr. Kieferorthop. 48: 59–66, 1987; Bell, W. H.; Mannai, C., Luhr, H. G., Art and science of the Le Fort I dolfracture Int. J. Adult Orthod. and Orthogn. Surg. 33: 23–52, 1988; Lindorf, H. H., Osteosynthese durch Schrauben und Miniplatten bei kieferorthopädischen Operationen. Inf. Orthod. Kieferorthop. 3: 329–350, 1988; Luhr, H. G. and Kubein-Meesenburg, D., Rigid skeletal fixation in maxillary osteotomies. Intraoperative control of condylar position. Clin Plast. Surg. 16: 157–163, 1989; Paulus, G. W., Moderne funktionelle und ästhetische Aspekte bei kieferorthopädischen Operationen. Inf. Orthod. Kieferorthop. 22: 33–55, 1990; Wangerin, K., Einzeitige bimaxilläre Korrektur extremer Fehlbisse-Vorbehandlung, Planung und Operationsmethode mit funktionsstabiler Fixierung im Ober- und Unterkiefer. Dtsch. Z. Mund. Kiefer Gesichtschir. 14: 424–432, 1990; Luhr, H. G., Schwestka, R., Kubein-Meesenburg, D., Intraoperative control of condylar position in maxillary osteotomies with rigid skeletal fixation. In: Bell W. H. (Hrsg): Modern practice in orthognathic and reconstructive surgery. Saunders, Philadelphia, at press).

First of all, in accordance with the preoperative planning, the cast surgery is carried out (Bell W. H., Proffit, W. R., White R. P., Surgical correction of facial deformities. 234–441, Saunders, Philadelphia, 1980; Epker, B. N., Fish, L. C., Dentofacial deformities. Integrated orthodontic and surgical correction. Mosby, St. Louis, 1986; Ehmer, U., Röhling, J. Dörr, K., Becker, R., Calibrated double split cast simulations for orthognathic surgery. Int. J. Adult Orthod. Orthognath Surg. 33: 223–227, 1988; Janson, I. and Steinhäuser, E. W., Kieferorthopädische Chirurgie - Eine interdisziplinäre Aufgabe. Quintessenz, Berlin, 1988; Jung, D., Datentransfer zwischen Artikulator und FRS zur Erstellung von diagnostischem Set up und VTO im komplexen Behandlungsfall. Inf. Orthod. Kieferorthop. 3: 383–395, 1988; Proffit, W. R. and White, R. P., Jr., Surgical-orthodontic treatment. Mosby, St. Louis, 1991). It is important, initially in a first articulator, to determine the exact pre-operative position of the maxilla and then in a second articulator to position exactly the desired post-operative position, since in accordance with the position in the second articulator the surgical splint is made with which in the surgical process the tooth-carrying maxillary segment is positioned in the planned position. Therefore, the cast or model surgery requires the greatest possible accuracy. Measurements with a ruler and the marking of reference points and reference lines on the base of the plaster cast above the tooth line of the maxilla model as well as the making of saw cuts in the base corresponding to these lines have not proved to be sufficiently accurate methods for the positioning of the maxillary segment. This is particularly so when the tooth-carrying maxillary segment has to be readjusted in several dimensions at the same time (Ellis, E. III., Accuracy of model surgery: Evaluation of an old technique and introduction of a new one. J. Oral Maxillofac. Surg. 48: 1161–1167, 1990). Therefore, various devices for the controlled adjustment of individual reference points on the teeth of the maxillary cast have been developed.

From the particularly eminent prior publication by Ellis E., III, Gallo, W. J., "A Method to Accurately Predict the Position of the Maxillary Incisor in Two-jaw Surgery", J. Oral. Maxillofac. Surg. 42: 402–404, 1984, a method for the exact positioning of one cutting edge of the upper incisors in the articulator in the sagittal-vertical plane is known, in which before the cast surgery a wire is wound around the incisal pin of the articulator in which the cast surgery is to be carried out, with the wire tip contacting the incisal edge of an upper incisor of the maxillary cast. This wire can be moved to one side during the cast surgery and then be repositioned thereafter in its final position. The distance between the tip of the wire and the new position of the edge of the upper incisor indicates the displacement of the incisor. This method is of limited use, because the wire tip is only adjusted to the pre-operative situation.

From the likewise eminent prior publication by Schwestka, R., Engelke, D., Zimmer, B., Kubein-Meesenburg, D., entitled "Positioning control of the upper incisors in orthognathic surgery. Pre-operative planning with the Model Positioning Device and intra-operative application of the Sandwich Splint", Eur. J. Orthodont. 13 367-371, 1991, another method is known. In this method, in the articulator, a measuring element is adjusted in a controlled manner in three dimensions with a model positioning unit to the pre-operative and also to the planned post-operative position of one incisal edge of a central incisor of the maxillary model. The relative spatial coordinate of each setting can be read off from scales.

Other authors have described methods used in cast surgery for the measurement successively in time of several different reference points on the teeth of the maxillary cast. These include on the one hand the use of a modified Boley measuring instrument in the articulator (Henry, C. H., "Modified Boley Gauge for use as a Reference Plan in Orthognathic Surgery", J. Oral Maxillofac. Surg. 48: 535-539, 1990), and on the other hand repeated shifting of the maxillary model on the Erickson measuring table outside the articulator (Ellis, E. III., "Accuracy of Model Surgery: Evaluation of an Old Technique and Introduction of a New One", J. Oral Maxillofac. Surg. 48: 1161-1167, 1990). The latter publication makes it clear that by the choice of reference points on the teeth of the maxillary model, on geometrical grounds the tolerance limits for positioning errors can be significantly reduced in comparison to the use of reference points on the base of the maxillary model.

During the surgery the planned position of the maxillary model is transferred to the skull. The position in the sagittal and transversal dimensions is determined by the surgical splint. The vertical dimension requires additional controls. Different authors develop different intra-operative methods for the exact adjustment in the vertical dimension (Austermann, K. H., and Bollmann, F., Eine Methode zur Bestimmung der günstigsten Osteotomieenbene bei Le-Fort-I-Osteotomien. Fortschr. Kiefer. Gesichtschir. 26: 121-123, 1981; Turvey, T. A., Simultaneous mobilization of the maxilla and mandible: Surgical technique and results. J. Oral Maxillofac. Surg. 40: 96-99, 1982; Johnson, D., Intraoperative measurement of maxillary repositioning: An ancillary technique. Oral Surg. Oral Med. Oral Pathol. 60: 266-268, 1985; Nishioka, G. J., and Van Sickels, J. E., Modified external reference measurement technique for vertical positioning of the maxilla. Oral Surg. Oral Med. Oral Pathol. 64: 22-23, 1987; Neubert, J., Bitter, K., Somsiri, S., Refined intraoperative repositioning of the osteotomized maxilla in relation to the skull and TMJ. J. Cranio-Max-Fac. Surg. 16: 8-12. 1988; Kahnberg, K-E., Sunzel, B., Astrand, P., Planning and control of vertical dimension in Le Fort I osteotomies. J. Cranio-Max-Fac. Surg. 18: 267-270, 1990). Clinical investigations into the question of the exact adjustment of the tooth-carrying maxillary segment in the vertical dimension show deviations between the pre-operative planned position and the intra-operative position actually achieved (Stanchina, R., Ellis, E., III, Gallo, W. J., Fonseca, R. J., A comparison of two measures for repositioning the maxilla during orthognathic surgery. Int. J. Adult. Orthod Orthognath. Surg. 33: 149-154, 1988; Van Nickels, J. E., Larsen, A. J., Epker, B. N., Predictability of maxillary surgery: A comparison of internal and external reference marks. Oral Surg. Oral Med. Oral Pathol. 61: 542-545, 1986). For these reasons, intra-operative positioning methods for a controlled three-dimensional adjustment of the tooth-carrying maxillary segment have been developed, by the use of a "sandwich splint" (Schwestka, R., Engelke, D., Kubein-Meesenburg, D., Luhr, H. G., Control of vertical position of the maxilla in orthognathic surgery: clinical application of the sandwich splint. Int. Adult Orthod. Orthognath. Surg. 5: 133-136, 1990; Schwestka, R., Röse, D., Kuhnt, D., Walloschek, W., Splint for controlling vertical position in maxillary osteotomies. J. Clin. Orthod 24: 427-431, 1990; Schwestka-Polly, R., Engelke, D., Kubein-Meesenburg, D., Luhr, H. G., Bedeutung der Vertikaldimension bei kieferorthopädischchirurgischen Eingriffen im Oberkiefer. Quintessenz 42: 595-601, 1991), or by the use of a "3D double splint method" in combination with a "Condylar positioning appliance (Schwestka, R., Engelke, D., Kubein-Meesenburg, D., Condylar position control during maxillary surgery: the condylar positioning appliance and three-dimensional double splint method. Int. J. Adult Orthod. Orthognath. Surg. 5: 161-165, 1990; Schwestka-Polly, R., Engelke, D., Kubein-Meesenburg, D., Gelenkorienteierte Einstellung des Oberkiefers mit der "Condylen-Positionierungs-Apparatur" im Rahmen der kieferorthopädischen Chirurgie. Quintessenz 42: 1099-1107, 1991). Both intra-operative methods are based upon the fact that the vertical position of the mandible in relation to the skull above the osteotomy plane is accurately reproducible in the pre-operative and post-operative situations. The vertical position of the mandible can be controlled intra-operatively with a pair of dividers. At this position of the mandible the tooth-carrying maxillary segment is adjusted three-dimensionally by means of the surgical splint as planned beforehand. Consequently, the position of the tooth-carrying maxillary segment planned during the cast surgery can be transferred exactly in three dimensions in a controlled manner during the actual surgical process. After the surgery the mandible is rotated up into the new intercuspidation position.

SUMMARY OF THE INVENTION

Accordingly, it is an object of the present invention to provide a method of three-dimensional adjustment of a maxillary model in an articulator for cast surgery, which improves the accuracy of the adjustment of the maxillary model in the articulator and consequently improves the surgical results.

In keeping with these objects and with others which will become apparent hereinafter, one feature of the present invention resides in a method of the above mentioned general type in which between the centering of the maxillary cast and the mandibular cast and a mobilization of the maxillary cast, three measuring elements of an adjusting device of an articulator part carrying the maxillary cast are each adjusted three-dimensionally into contact with respective reference points on teeth of the maxillary cast and the relative spatial coordinates of each reference point are established, between the adjustment of the mobilized maxillary cast three-dimensionally in the articulator and the mobilization of the maxillary cast the height of the base of the maxillary cast is changed, before the adjustment of the mobilized maxillary cast three-dimensionally in the articulator the three measuring elements are adjusted three-dimensionally to the desired post-operative positions of the reference points, and during the adjustment of the mobilized maxillary cast it is supported at its reference points on the three measuring elements, while before making the surgical splint the mobilized maxillary cast is secured again to the articulator part in its position in which it is supported at its reference points.

As the articulator one can use in particular a semi-individually adjustable articulator, or example from the firm SAM, Taxistrasse 41, W-8000 Munich 19. The three reference points on the teeth of the maxillary model lie at a sufficient distance from each other and are each marked on the teeth, for example by means of color markings or small borings. The relative spatial coordinates of each of these reference points are determined very accurately in the pre-operative situation, for example by reading them off scales of the adjusting device. The height change can be effected for example by first making a substantially horizontal saw cut through the base of the maxillary model which is made for example as a plaster cast. Supplementary to this, at least one of the resulting sawn surfaces can be ground down until overall the desired height change of the maxillary model has been achieved. This height change can take place in any manner, as it were "free hand", and in particular is not connected with the adjustments and measurements conventional until now for model surgery involving a ruler, the marking of reference points and osteotomy lines on the base and the subsequent cutting along these osteotomy lines on the plaster model. This simple height adjustment of the maxillary model brings about a very considerable simplification and shortening of the phase of the cast surgery in the articulator. The previously conventional saw cuts on the plaster model according to marked lines are subject moreover to inaccuracies which subsequently lead to unsatisfactory results in the surgery itself. In contrast to this, according to the invention, in the pre-operative planning, displacement paths for the three reference points are established, and indeed starting from the spatial positions of the reference points in the pre-operative situation. These displacement paths result from the pre-operative planning data, for which in particular the model, remote X-ray pictures and profile plottings in the ratio 1:1 are relevant. The remote X-ray pictures give information about the osseous structure of the patient and the profile plottings essentially give guide points from aesthetical points of view, above all the position of the incisal edges of the upper central incisors relative to the upper lip of the patient. The three measuring elements are adjusted three-dimensionally to the desired post-operative positions of the reference points having regard to the pre-planned displacement paths of the reference points. This is effected preferably with the aid of scale values of the adjusting device which are reproducible and with extraordinary precision. The supporting of the mobilized maxillary model can be effected for example either in a force-locking manner at color-marked reference points, or alternatively in a shape-locking manner in small bores in the maxillary cast at these reference points. In each case one can achieve a mobilized maxillary cast located within the articulator exactly in the desired post-operative position. This desired position is then preserved. The subsequent making of the surgical splint follows with corresponding precision with good prospects of corresponding intra-operative results.

Additionally, the maxillary cast can be segmented outside the articulator and its dental arch is brought into the desired post-operative form. This is of especial value with maxillae which are too narrow. By the segmentation the maxilla is initially widened to the desired degree and then can be further treated according to the method of the invention.

Preferably a first reference point is located at least approximately on the incisal edge of an upper central incisor and each further reference point is located at least approximately on the biting surface of an upper-right and upper-left molar respectively. This positioning of the three reference points has proved to be particularly favorable. Preferably, the two lateral reference points lie on the mesiobuccal cusps of the first molars. In this way the three reference points are located at a sufficient distance from one another in regions of the dental arch which are easily accessible from the outside.

Preferably one examines whether the maxillary cast is located in its desired post-operative position relative to the mandibular cast, and if this is not the case, the position of one or more of the measuring elements is corrected by three-dimensional adjustment. This offers particular advantages and leads to an especially precise relative positioning of maxillary and mandibular dental arches.

Preferably, in accordance with the last-mentioned preferred feature each measuring element is adjusted in or at right-angles to a reference plane, and the reference plane extends through or parallel to a hinge axis of the jaw hinge of the articulator. In this way the spatial coordinates of the measuring elements can be adjusted particularly simply, precisely and reproducibly.

If the reference plane is the hinge axis-infraorbital plane then this has proved to be particularly advantageous for the practical working in the articulator.

The invention also is concerned with a method for making of a further surgical splint as an aid to the positioning of the tooth-carrying maxillary and mandibular segments to be mobilized in a later bimaxillary surgical treatment, as a supplement to the surgical splint of the invention referred to above.

In one known method of this type disclosed in the German reference DE 4,018,273 A1 the three-dimensional adjustment of the mandibular segment 37 is carried out in a special way.

It is a further object of the invention, in a method according to the invention, to facilitate, to speed up and to improve the three-dimensional adjustment of the mandibular cast.

This object is achieved in that the maxillary cast is adjusted three-dimensionally in the articulator into the desired post-operative dental situation relative to the pre-operative planned position of the upper lip of the patient and relative to the rest of the skull of the patient and then is fixed to the associated articulator part, a mandibular cast is mobilized, the height of a base of the mandibular cast is changed, the dental arch of the mandibular cast created from the preceding step is adjusted relative to the dental arch of the adjusted maxillary cast into the desired post-operative dental situation, the mobilized mandibular cast is fixed again to another articulator part in its position created from the preceding step, and on the basis of the relative adjustment of maxillary cast and mandibular cast achieved according to the preceding step the further surgical splint is made in a gap between maxillary cast and mandibular cast for analogous intra-operative use.

In this method, an ideal relative position of the mobilized mandibular cast relative to the already repositioned maxillary cast is guaranteed. The thus located position of the mandibular cast is fixed and is used for the production of a further perfect surgical splint. By this means, optimum results can again be anticipated for the intra-operative positional correction of the mandible.

Preferably, before the adjustment of the dental arch the articulator is rotated downwards with the maxillary cast. This make use of gravity for the relative positioning of the mandibular cast in relation to the maxillary cast.

Particular advantages can be achieved if the adjustment of the dental arch is effected in such a manner that the dental arch of the mobilized mandibular cast is located on the dental arch of the maxillary cast.

Preferably, the fixing is effected by plaster ties. The plaster ties have proved to be a particularly simple and functionally reliable way of fixing the jaw parts which have up to then been mobilized. In the height adjustment of the maxillary cast and of the mandibular cast in the region of the associated base the respective mounting plates on the one hand and the respective jaw casts on the other hand remain unimpaired. The intermediate space between the two resulting from the height adjustment and subsequent repositioning of the mobilized jaw casts is reliably maintained again by this means.

The invention is also concerned with an apparatus, namely a so-called "Model Positioning Appliance" for the three-dimensional adjustment of a maxillary cast in an articulator, in which by means of an articulator part associated with the maxillary cast a reference plane is defined which extends through or parallel to a hinge axis of the jaw hinge of the articulator.

In this apparatus a first guide member extending perpendicular to the reference plane is mounted on the articulator part, a second guide member is displaceable along the first guide member and is securable thereon, a holder is displaceable relative to the second guide member parallel to the reference plane from anterior and posterior and vice versa and is securable thereto, and the holder comprises a first measuring element displaceable perpendicular to the direction of displacement of the holder and parallel to the reference plane and is securable to the holder, said measuring element being adjustable to a first reference point which is at least approximately on the incisal edge of an upper central incisor of the maxillary cast.

One known apparatus of this type is known from the publication of Schwestka et al., 1991 previously referred to above. This appliance is only equipped with a single, three-dimensionally adjustable measuring element, which cooperates with a reference point on a central incisor of the maxillary cast. This known appliance has only a limited range of use and is also only appropriate for isolated maxillary surgery.

It is therefore also an object of the invention, in an apparatus of this type, to improve the accuracy and the range of use of the adjustment of the maxillary cast in the articulator and consequently, as a secondary aspect, to improve the surgical results.

this object is achieved in an apparatus of this type in which the holder has a third guide member and a fourth guide member which each extend parallel to the direction of displacement of the holder on opposite sides of the maxillary cast, in which a fifth guide member and a sixth guide member are each displaceable along the third guide member and fourth guide member respectively and are securable thereto, in which a seventh guide member and an eighth guide member are respectively displaceable relative to the fifth guide member and the sixth guide member at right-angles to the reference plane and are securable thereto, and in which a second measuring element and a third measuring element are adjustable relative to the seventh guide member and eighth guide member respectively transversely to the direction of displacement of the holder to a second reference point and a third reference point respectively on opposing molars of the maxillary cast and are securable to the respective guide members.

The hinge axis-infraorbital plane serves particularly well as the reference plane. The adjustment movements are executed either parallel to this reference plane or at right-angles to it. The establishment of the relative spatial coordinates of each reference point is facilitated if scales are positioned on the apparatus elements which are displaceable relative to each other, with the particular measured value being readable from the scales and then documented. The buccal reference points are preferably located on the mesiobuccal cusps of the first upper molars. The apparatus permits a simple, rapid and reliably reproducible three-dimensional adjustment of all measuring elements both in the pre-operative situation and also in the desired post- 0 operative situation of the maxillary cast.

Preferably, the first guide member is secured to an arm and is arranged outside a longitudinal central plane of the articulator which is perpendicular to the hinge axis. According to this feature clear vision and ease of access to the rows of teeth from the front in the articulator is facilitated.

Preferably, the apparatus is one in which the holder includes a ninth guide member which extends perpendicular to the direction of displacement of the holder and parallel to the reference plane and in which the first measuring element is displaceable along the ninth guide member and is securable thereto. By these features the adjustment of the first measuring element is made easier.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
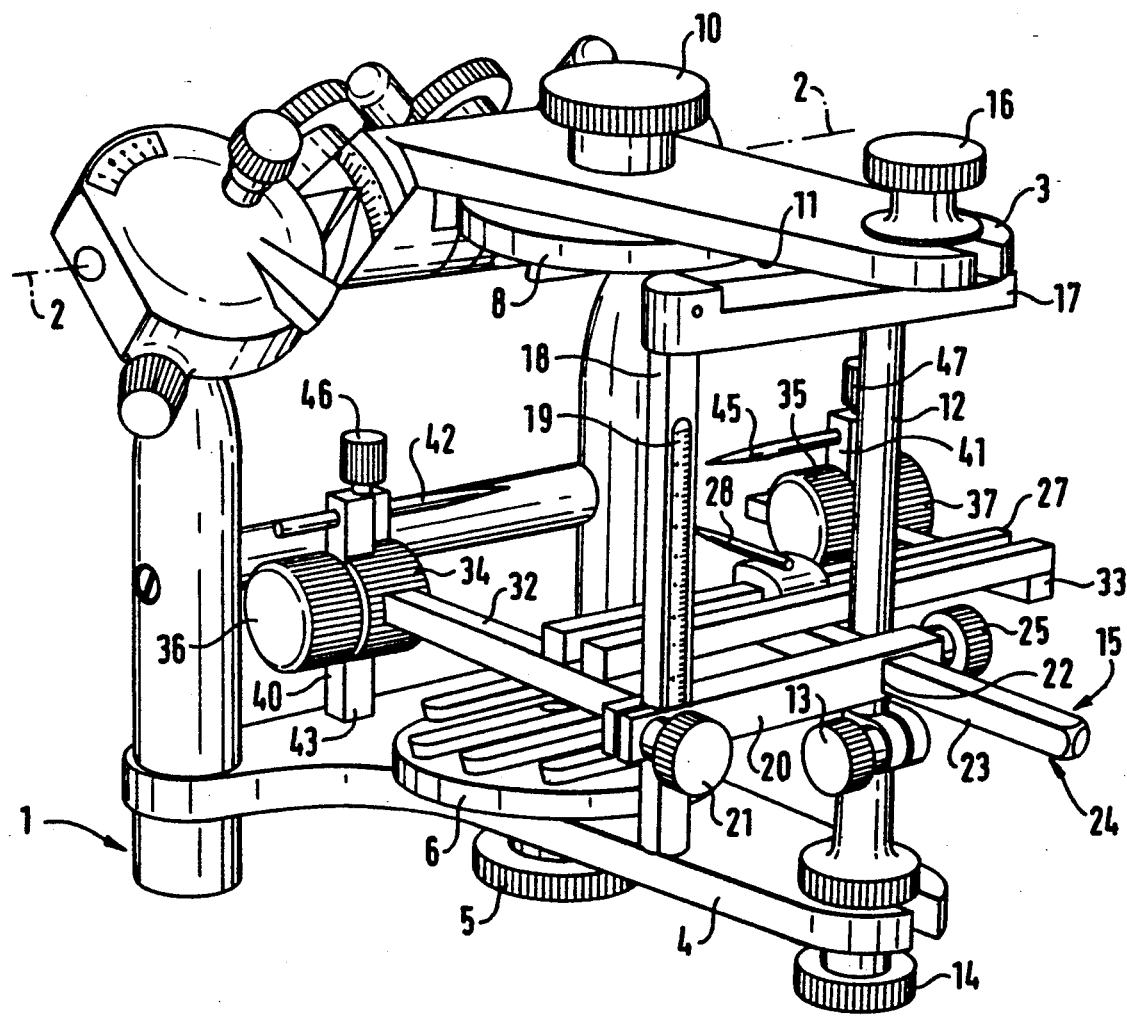
FIG. 1 is a perspective view of an articulator with the appliance or "Model Positioning Appliance" mounted therein.

FIG. 1 shows a semi-individual adjustable articulator 1 comprising a first articulator part 3 which an be raised and lowered about a pivot axis 2 and a second articulator part 4 which in this case is the lower part.

Figure 5:
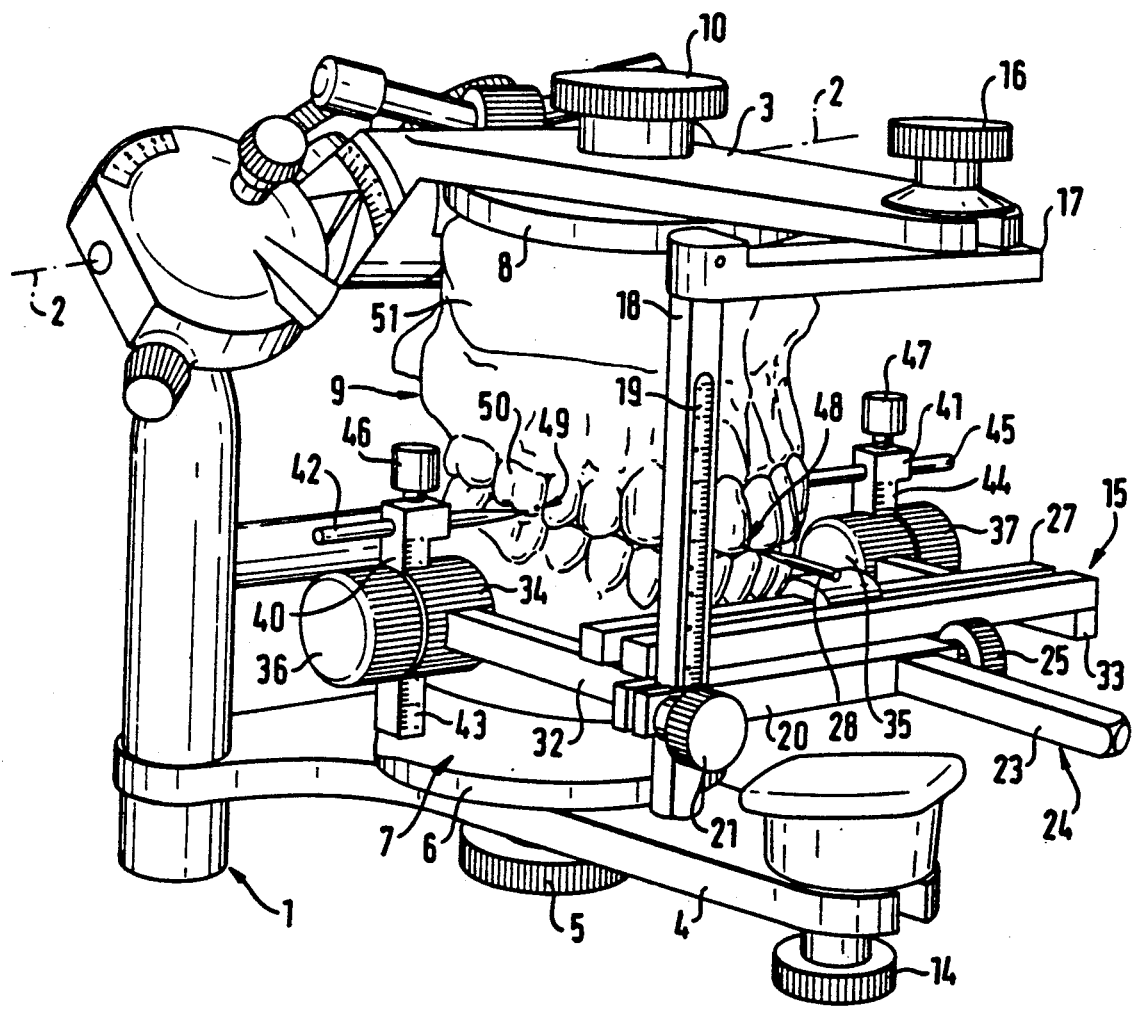
FIG. 5 is a perspective view of the apparatus of FIG. 1 with a pair of casts in the pre-operative position.

The second articulator part 4 includes as a rule a base support which is not shown in FIG. 1. It carries a mounting plate 6, releasable by a screw 5, for a mandibular cast 7 (FIG. 5). In a similar manner, on the first articulator part 3 a mounting plate 8 for a maxillary cast 9 (FIG. 5) is releasably secured by means of a screw 10.

The underside of the articulator part 3 defines a reference plane 11 which extends through or parallel to the hinge axis 2 of the articulator 1. The reference plane 11 is preferably the hinge axis-infraorbital plane.

Normally, the articulator part 3 rests on a vertical support pin 12 which in a manner known per se can be adjusted as to its height by means of a screw 13 and which is mounted releasably on the other articulator part 4 by means of a further screw 14.

In the reference plane 11, with the support pin 12 removed as a rule, there is releasably secured by means of a screw 16 a device 15 for the three-dimensional adjustment of the maxillary cast 9.

An arm 17 of the device 15 extends in the reference plane 11 in FIG. 1 to the left and carries at its free end a downwardly extending first guide member 18 which is perpendicular to the reference plane 11. The first guide member 18 is of essentially rectangular cross-section and is equipped with a scale 19 in its longitudinal direction. A second guide member 20 which extends to the right parallel to the reference plane in FIG. 1 is displaceable along the first guide member 18 and can be fixed in place by clamping screw 21.

At its free end the second guide member 20 has a square hole 22 (see also FIG. 2) which extends parallel to the reference plane 11 from the anterior to the posterior. The hole 22 displaceably receives a rod 23 (see also FIG. 3) of a holder 4 and can be fixed in place by a clamping screw 25. The direction of displacement 26 of the holder 24 is indicated in FIG. 3 by a double-headed arrow.

Figure 3:
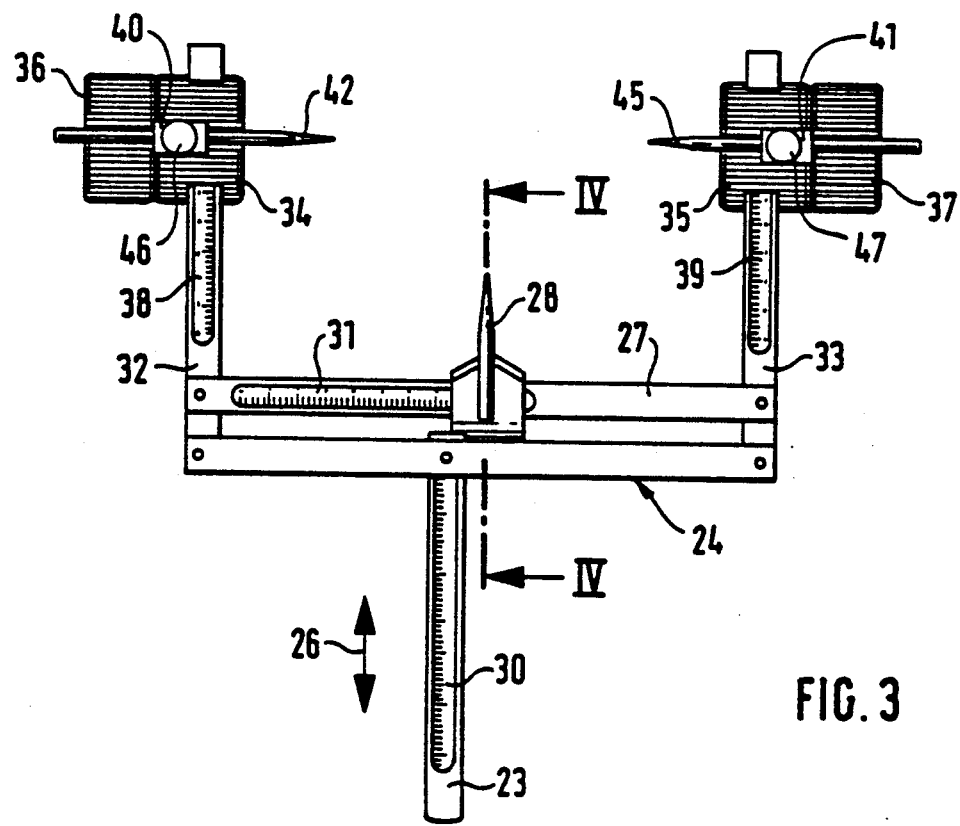
FIG. 3 shows a part of the apparatus of FIG. 1, viewed from above.
Figure 4:
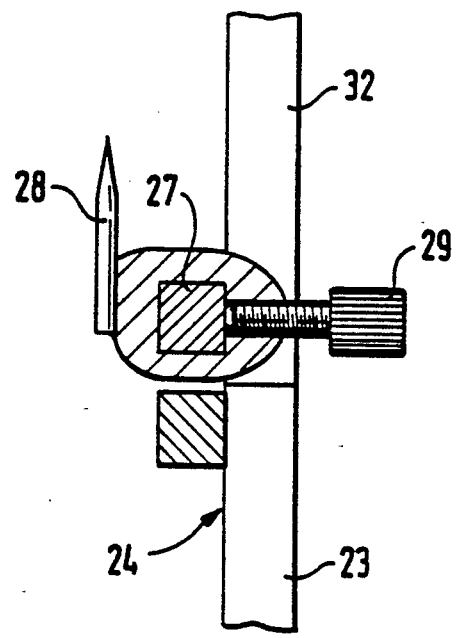
FIG. 4 is the sectional view taken along the line IV—IV in FIG. 3.

The holder 24 includes a ninth guide member 27 which extends parallel to the reference plane and at right-angles to the direction of displacement 26 of the holder 24. A first measuring element 28 is displaceable along the ninth guide member 27 and can be fixed in place by a clamping screw 29 (FIG. 4). On the rod 23 is provided a scale 30 from which the particular displacement setting of the holder 24 in the direction of displacement 26 can be read off (FIG. 3). In a similar manner, the ninth guide member 27 carries a scale 31 from which can be read off the displaced position of the first measuring element 28 (FIG. 3).

The holder 24 also includes a third guide member 32 and a fourth guide member 33 which each extend parallel to the direction of displacement 26 (FIG. 3) of the holder 24 and (FIG. 5). A fifth guide member 34 nd a sixth guide member 35 are respectively displaceable along the third guide member 32 and along the fourth guide member 33 and can be respectively fixed in place by clamping screws 36 and 37. The respective displacement settings of the fifth guide member 34 and of the sixth guide member 35 can be read off from associated scales 38 and 39 (FIG. 3).

A seventh guide member 40 and an eighth guide member 41 are displaceable perpendicular to the reference plane and respectively relative to the fifth guide member 34 and the sixth guide member 35. The seventh and eighth guide members 40, 41 can be fixed in place by respective clamping screws 36 and 37. The particular displacement settings of the seventh and eighth guide members 40, 41 can be read off from the scales 43 and 44 (FIG. 5).

A second measuring element 42 and a third measuring element 45 are displaceable relative to the seventh and eighth guide members 40, 41 respectively. They are displaceable transversely to the direction of displacement 26 of the holder 24 and can be fixed in place by clamping screws 46 and 47 respectively.

A longitudinal central plane of the articulator extends perpendicular to the hinge axis 2 and passes through the longitudinal axes of the support pin 12 and of the screws 14 and 16.

Figure 2:
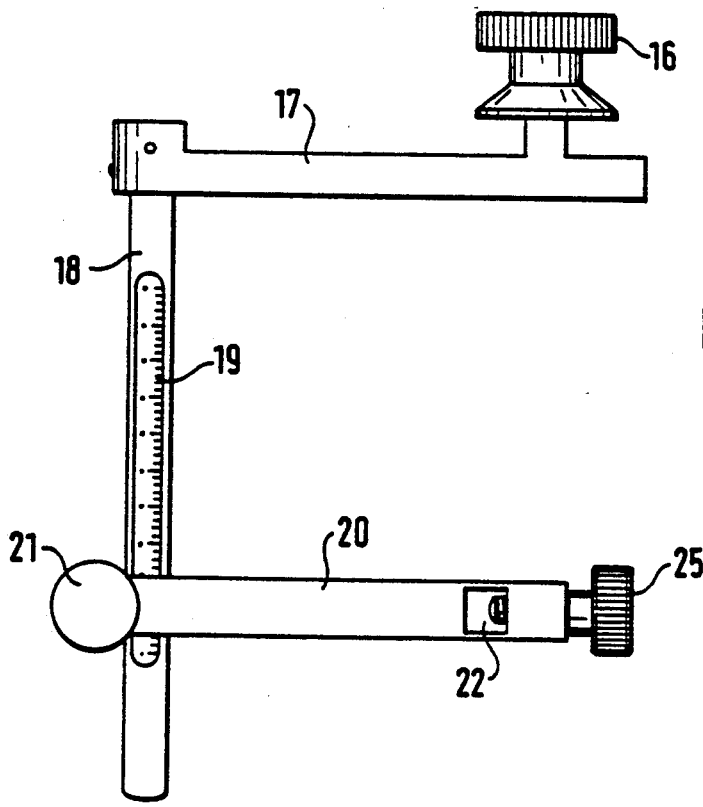
FIG. 2 shows a part of the apparatus of FIG. 1, viewed from the front.

FIG. 2 shows particularly clearly that the first guide member 18 is located with a lateral spacing from this longitudinal central plan and consequently facilitates the view into the articulator 1 and the access into it from anterior and posterior.

The cross-section of the majority of the guide members referred to above is non-circular, preferably rectangular, in order to prevent a rotation of the components carried by the guide members and also to facilitate the three-dimensional adjustment of the device 15, as will be described hereinafter.

FIG. 3 shows clearly that the scales 30, 31, 38, 39 can all be read from above, wile the scales 19, 43 and 44 are to be read from the posterior direction. This facilitates the rapid and reliable reading of each displacement setting and the associated displacement adjustments to predetermined scale values.

FIG. 4 shows details of the holder 24 and of the first measuring element 28 including its method of securement to the ninth guide member 27.

The method of working with the apparatus 15 will now be described with reference to one example.

The pair of casts consisting of the mandibular cast and the maxillary cast 9 made at least approximately in the ratio 1:1 is mounted in the articulator in a centered position with reference to the hinge axis 2 with the aid of a facebow transfer and bite registration. The mandibular cast 7 and the maxillary cast 9 are then located in the pre-operative dental situation which is shown in FIG. 5. Then, the support pin 12 shown in FIG. 1 is removed and the apparatus 15 is secured to the articulator part 3 by means of the screw 16. The second and third measuring elements 42 and 45 are each drawn sufficiently far outwards that they do not come into contact with the pair of casts 7 and 9. Then, the free tip of the first measuring element 28 is moved three-dimensionally into contact with a first reference point 48 adjacent to the incisal edge of a central incisor of the maxillary cast 9 (see also FIG. 6). Depending upon the required three-dimensional movement, this is effected by displacement of the second guide member 20 on the first guide member 18 and/or by displacement of the rod 23 of the holder 24 relative to the second guide member 20 and/or by displacement of the first measuring element 28 on the ninth guide member 27. As soon as the first measuring element 28 contacts the first reference point 48, all the aforementioned adjustment possibilities are fixed. Then, the second and third measuring elements 42 and 45 are moved three-dimensionally in succession into contact with respective further lateral reference points 49 on a first molar 50 of the maxillary cast 9. As required, this is effected by the seventh and eighth guide members 40 and 41 being displaced relative to the fifth and sixth guide members 34 and 35 and/or by the measuring elements 42 and 45 being displaced relative to the seventh and eighth guide members 40 and 41. The final resulting relative position of these parts of the apparatus is fixed. The measuring elements 28, 42 and 45 thus stand with their tips at the associated reference points 48 and 49 of the maxillary cast 9. The scale values pertinent to this three-dimensional adjustment of the apparatus 15 are then read off and noted.

By pre-operative planning, any departure of the thereby established actual coordinate of the three reference points, for example 48 and 49, from their desired coordinates is established. It means also that now the maxillary cast 9 can be brought into a position corresponding to these desired coordinates.

For this, first the appliance 15 is removed by removing the screw 16 from the articulator 1. Then, without the previous establishment of osteotomy lines on a base 51 of the maxillary cast 9, a saw cut is made extending approximately parallel to the reference plane. By this means the mounting plate 8 is left with the upper part of the base 51 at its position and a lower part of the base 51 is mobilized with the maxillary cast 9. The separating surface on the base part of the maxillary cast 9 thus created can, as required, by smoothed off somewhat, so that sufficient free space is made available for the three dimensional adjustment movements of the maxillary cast 9.

Then, the appliance 15 is again fixed by means of the screw 16 to the articulator part 3. Following this, in the manner analogous to that already described above, first of all the first measuring element 28 is adjusted three-dimensionally into the aforementioned desired position and after this the second and third measuring elements 42 and 43 are adjusted likewise. The tips of the measuring elements 28, 42, 45 then define the desired position of the maxillary cast corresponding to the pre-operative planned situation and the post-operative situation to be achieved. The mobilized maxillary cast 9 is thus supported at its three reference points, for example 48 and 49, by the tips of the measuring elements 28, 42 and 45.

It is of special advantage that in the thus produced, desired post-operative position of the maxillary cast 9 the relative spatial position of the maxillary cast 9 in relation to the mandibular cast 7 can be checked. If any small discrepancies should be found, since the mandibular cast in this case represents the reference structure, the position of the maxillary cast 9 can still be corrected to the necessary degree which can be the most trifling amount. This correction is effected by appropriate three-dimensional readjustment of the measuring elements 28, 42 and 45.

When in this way the desired position of the maxillary cast 9 is finally established, the maxillary cast 9 is again fixed to the articulator part 3. This is effected preferably by fixing plaster ties of the lower base part of the maxillary cast 9 to the now present upper base part of the mounting plate 8.

Finally, in a gap between the maxillary cast 9 and the mandibular cast 7, which is formed by upward rotation of the maxillary cast 9 about the hinge axis 2, surgical splint for analogous intra-operative use is made.

Figure 8:
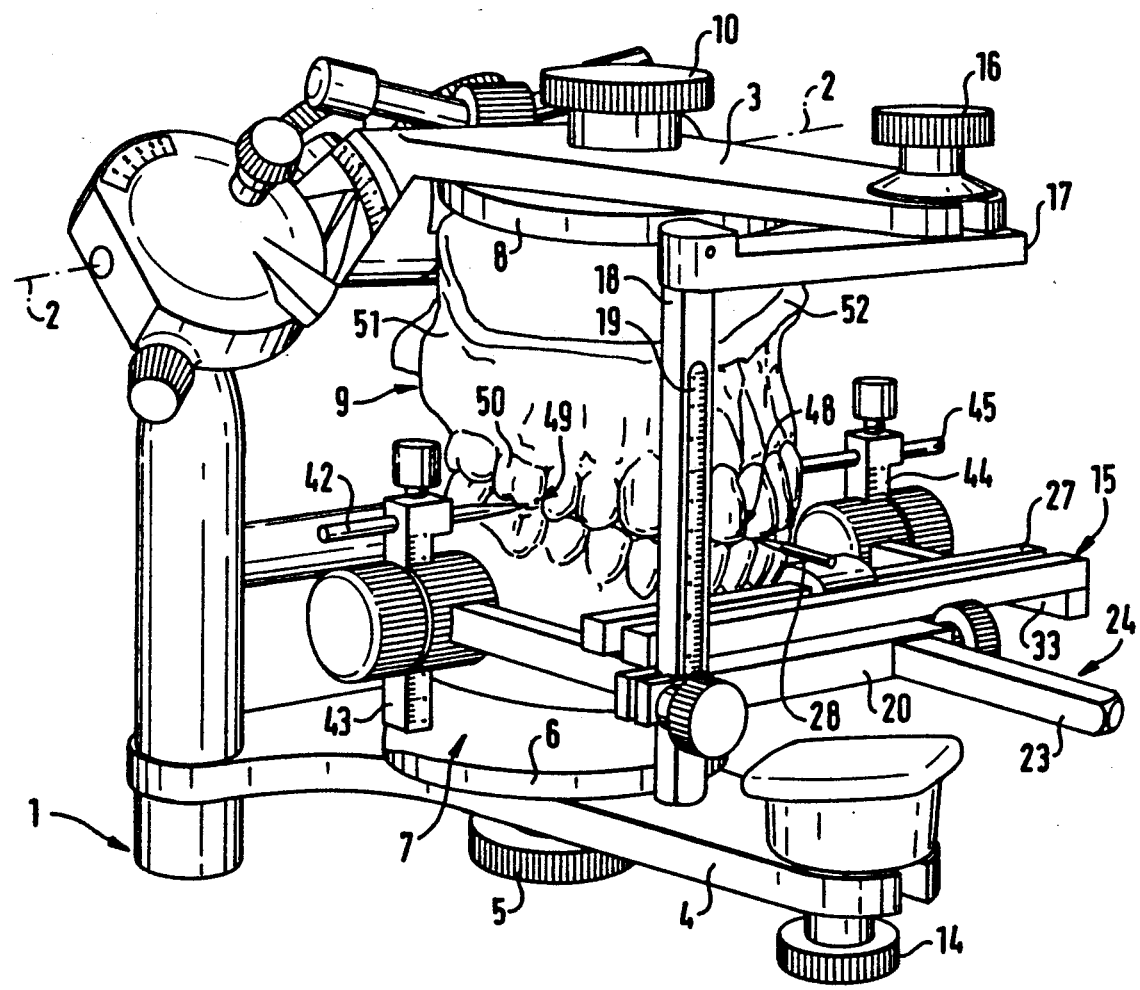
FIG. 8 is a perspective view of the apparatus corresponding to FIG. 5 with the inserted pair of casts in the post-operative position.

FIG. 8 shows the above described desired position of the maxillary cast 9, with a plaster layer 52 in the region of the base 51 denoting that zone in which the maxillary cast 9 has been plastered in its desired position again to the upper part of the base 51.

The scales on the different parts of the appliance 15 facilitate the adjustment of the desired positions of the measuring elements 28, 42 and 45.

Figure 6:
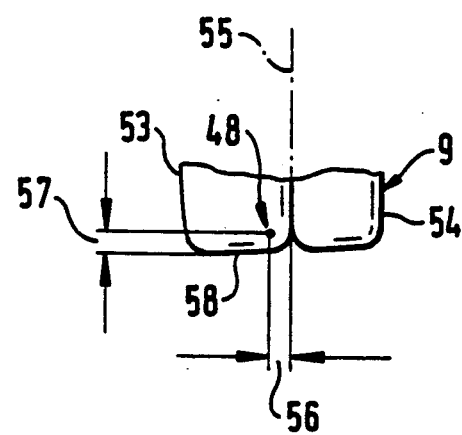
FIG. 6 shows a referee point on an upper central incisor.

FIG. 6 shows central incisors 53 and 54 of the maxillary cast 9. Also shown is the sagittal-vertical plane 55 from which the first reference point 48 should be only the smallest possible distance 56 away. Correspondingly, the first reference point 48 should only be the smallest possible distance 57 from an incisal edge 58 of the incisor 53. By this positioning of the first reference point 48 one ensures that even after complex, three-dimensional repositioning movements of the maxillary cast 9 the incisal edge 58 is located in the final desired position relative to the upper lip of the patient and in relation to the rest of the skull.

Figure 7:
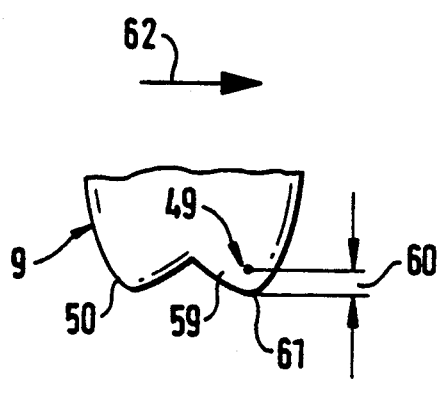
FIG. 7 shows a further reference point on a molar.

FIG. 7 indicates the position of the further reference point 49 on the mesiobuccal cusp 59 of the first molar 50 of the maxillary cast 9. The further reference point 49 should be the smallest possible distance 60 from a cusp tip 61. The anterior direction is indicted in FIG. 7 by an arrow 62.

The referee points, for example 48 and 49, can be fixed either by color markings or alternatively by small borings at the indicated positions in the maxillary cast 9. In the first case one has a force-locking connection with the measuring elements 28 and 42 and 45 and in the latter case a shape-locking connection.

As mentioned above, with isolated treatment in the maxilla, the dental arch of the mandibular cast 7 defines the position of the maxillary cast 9 in the sagittal and transversal dimensions. Here, having priority, the vertical position of the maxillary cast 9 is defined by the appliance 15.

In the case of bimaxillary surgery the maxilla is operated on first in the manner described. Here, a positional control is more difficult and is necessary in the sagittal, transversal and vertical dimensions, because with bimaxillary surgery the position of the dental arch in the mandible is also changed and this can no longer serve as a reference for the surgical end situation.

In the case of a planned bimaxillary surgery, first of all the maxillary cast 9 is adjusted into its new desired position corresponding to the desired post-operative situation in the manner described above. Then, the appliance 15 is again removed from the articulator part 3 and the mandibular cast 7 is mobilized by a separating cut through its base. At least one of the thus created base separating surfaces can, as necessary, be somewhat smoothed, until the mandibular cast 7 has the free space for movement which is necessary for its re-positioning. Then, in a suitable manner the articulator 1 is set on the head, so that the maxillary cast 9 is positioned at the bottom. The mobilized mandibular cast is then set with its dental arch on the dental arch of the maxillary cast 9, until the optimum relative position is found. In this optimum position the mandibular cast 7 is again fixed, preferably again by means of plaster ties, to the base part which is connected to the mounting plate 6.

Consequently, the optimum, pre-operative planned position is achieved for the maxillary cast 9 and the mandibular cast 7, in which position by outward rotation of the maxillary cast 9 a small gap can be made between the casts and the surgical splint.

As indicated already, the apparatus is also appropriate for use with segmented maxillae. For this, first of all the dental arch of the maxillary cast 9 is adjusted into the desired post-operative situation and then the cast is divided outside the articulator 1 by previously planned saw cuts. The parts are adjusted into the desired positions relative to one another and are fixed with plaster. The thus altered maxillary cast is then introduced into the articulator 1 for the three-dimensional positioning in the manner already described above.

It will be understood that each of the elements described above, or two or more together may also find a useful application in other types of methods and constructions differing from the types described above.

While the invention has been illustrated and described as embodied in a method and apparatus for three-dimensional adjustment of maxillary model in articulator for cast surgery, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. An apparatus for three-dimensional adjustment of a maxillary cast in an articulator having an articulator part associated with the maxillary cast, in which by means by the articulator part a reference plane is defined which extends through or parallel to a hinge axis of a jaw hinge of the articulator, the apparatus comprising a first guide member extending perpendicular to the reference plane and mounted on the articulator part; a second guide member displaceable along the first guide member and securable thereon; a holder displaceable relative to the second guide member parallel to the reference plane from anterior and posterior and vice versa an securable to said second guide member, said holder comprising a first measuring element displaceable perpendicular to a direction of displacement of said holder and parallel to the reference plane and securable to said holder, said first measuring element being adjustable to a first reference point which is at least approximately on an incisal edge of an upper central incisor of the maxillary cast; and a third guide member and a fourth guide member provided on said holder and each extending parallel to the direction of displacement of said holder on opposite sides of the maxillary cast; a fifth guide member and a sixth guide member each displaceable along the third guide member and the fourth guide member respectively and securable to them; a seventh guide and an eighth guide member respectively displaceable relative to said fifth guide member and said sixth guide member at right angles to the reference plane and securable to said fifth guide member and said sixth guide member; a second measuring element and a third measuring element adjustable relative to said seventh guide member and said eighth guide member respectively transversely to the direction of displacement of said holder to a second reference point and a third reference point, respectively, on opposing molars of the maxillary cast and securable to said seventh guide member and said eighth guide member respectively.

2. An apparatus as defined in claim 1, wherein said first guide member is secured to an arm and is arranged outside a longitudinal central plane of the articulator which is perpendicular to the hinge axis.

3. An apparatus as defined in claim 1; and further comprising a ninth guide member provided on said holder and extending perpendicularly to the direction of displacement of said holder and parallel to the reference plane, said first measuring element being displaceable along said ninth guide member and being securable to said ninth guide member.

4. A method of making a surgical splint as an aid to positioning of a tooth-carrying maxillary segment which is to be mobilized following Le Fort I surgery, the method comprising the steps of centering a maxillary cast and a mandibular cast of a pair of casts of a patient made at least approximately in the ratio 1:1 in an articulated manner in an articulator with reference to a jaw hinge so as to adjust into a pre-operative dental position; mobilizing the maxillary cast; adjusting the mobilized maxillary cast three-dimensionally in the articulator into a desired post-operative dental position relative to the pre-operative planned position of an upper lip of the patient and relative to the rest of the pair of casts; on the basis of the relative adjustment of the maxillary cast and mandibular cast achieved according to the immediately preceding step, making a surgical splint in a gap between the maxillary cast and the mandibular cast for analogous intra-operative use; between the centering and the mobilizing, adjusting three measuring elements of an adjusting device of an articulator part carrying the maxillary cast each into contact with respective reference points on teeth of the maxillary cast, and establishing relative spatial coordinates of each reference point; between the mobilizing the maxillary cast and adjusting the mobilized maxillary case changing a height of a base of the maxillary cast; before adjusting the mobilized maxillary cast, adjusting the three measuring elements three-dimensionally to the desired post-operative positions of the reference points; during adjusting the mobilized maxillary cast, and after the changing of the height of the base of the maxillary cast, supporting the mobilized maxillary cast at its reference points on the three measuring elements; and before making the surgical splint, securing the mobilized maxillary cast again to the articulator part in the position created from the adjustment of the mobilized maxillary cast.

5. A method as defined in claim 1; and further comprising the step of segmenting the maxillary cast outside the articulator and bringing its dental arch into the desired post-operative form, between the mobilizing of the maxillary cast and changing the height of the base of the maxillary cast.

6. A method as defined in claim 1; and further comprising the step of locating a first reference point at least approximately on an incisal edge of an upper central incisor and locating each further reference point at least approximately on a biting surface of an upper-right and upper-left molar respectively.

7. A method as defined in claim 1; and further comprising the step of examining whether the maxillary cast is located in its desired post-operative position relative to the mandibular cast, between the supporting of the mobilized maxillary cast at its reference points and securing the mobilized maxillary cast again to the articulator part; and if this is not the case, correcting the position of one or more of the measuring elements by three-dimensional adjustment.

8. A method as defined in claim 1, wherein said adjusting of the measuring elements includes adjusting each of the measuring elements in or at right angles to a reference plane which extends through or parallel to a hinge axis of a jaw hinge of the articulator.

9. A method as defined in claim 8, and further the step of choosing the reference plane to be a hinge axis-infraorbital plane.

10. A method as defined in claim 1; and further comprising the step of making a further surgical splint as an aid to positioning of the tooth-carrying maxillary and mandibular segments to be mobilized in a later bimaxillary surgical treatment, as a supplement to the surgical splint made according to claim 1, said making including adjusting the maxillary cast three-dimensionally in the articulator into the desired post-operative dental position relative to pre-operative planned position of the upper lip of the patient and relative to the rest of the skull of the patient, and then fixing to an associated articulator part; mobilizing a mandibular cast again; changing the height of the base of the mandibular cast again; adjusting a dental arch of the mandibular cast created in the immediately preceding step, relative to a dental arch created from the adjustment of the maxillary cast, into the desired post-operative dental situation fixing the mobilized mandibular cast again to another articulator part in its position created from dental arch; and on the basis of the relative adjustment of the maxillary cast and mandibular cast achieved in the immediately preceding step, making the further surgical splint in a gap between the maxillary cast and the mandibular cast for analogous intra-operative use.

11. A method as defined in claim 10, wherein said fixings are effected by plaster ties.

12. A method as defined in claim 1; and further comprising the step of rotating the articulator downwardly with the maxillary cast before adjusting the dental arch.

13. A method as defined in claim 12, wherein said adjustment of the dental arch of the mandibular cast is effected so that the dental arch of the mobilized mandibular cast is located on the dental arch of the maxillary cast.

* * * * *